United States Patent [19]

Champain et al.

[11] Patent Number: 4,827,922

[45] Date of Patent: May 9, 1989

[54] PROCESS AND DEVICE FOR SUPPLYING RESPIRATORY OXYGEN

[75] Inventors: Roger Champain, Les Loges en Josas; Gilbert Theurant, Vitry-sur-Seine, both of France

[73] Assignee: L'Air Liquide, Paris, France

[21] Appl. No.: 163,517

[22] Filed: Mar. 2, 1988

[30] Foreign Application Priority Data

Mar. 5, 1987 [FR] France ................................ 87 02978

[51] Int. Cl.⁴ .......................................... A61M 16/00
[52] U.S. Cl. ........................ 128/204.21; 128/204.28; 128/204.26; 128/204.29
[58] Field of Search ...................... 128/204.28, 204.21, 128/204.18, 204.23, 204.26, 204.29

[56] References Cited

FOREIGN PATENT DOCUMENTS 0093503 11/1983 European Pat. Off. .
0183593 11/1985 European Pat. Off. .
8417236 5/1986 France .
131032 2/1986 Japan .
06969 12/1986 PCT Int'l Appl. .
01412 7/1988 PCT Int'l Appl. .
2178193 2/1987 United Kingdom .

Primary Examiner—Edgar S. Burr
Assistant Examiner—Aaron J. Lewis
Attorney, Agent, or Firm—Lee C. Robinson, Jr.

[57] ABSTRACT

The invention relates to the supply of superoxygenated air to a patient during a part of the inspiratory phase. An electrically controlled supply valve is opened as soon as the sensor of a detector receives a depression signal due to a start of inspiration. This produces a voltage which is compared with a reference voltage corresponding to the atmospheric pressure previously stored in a memory. The duration of the injection is counted and is proportional to the duration of the non-injection which is dependent on the duration of the expiratory phase.

13 Claims, 1 Drawing Sheet

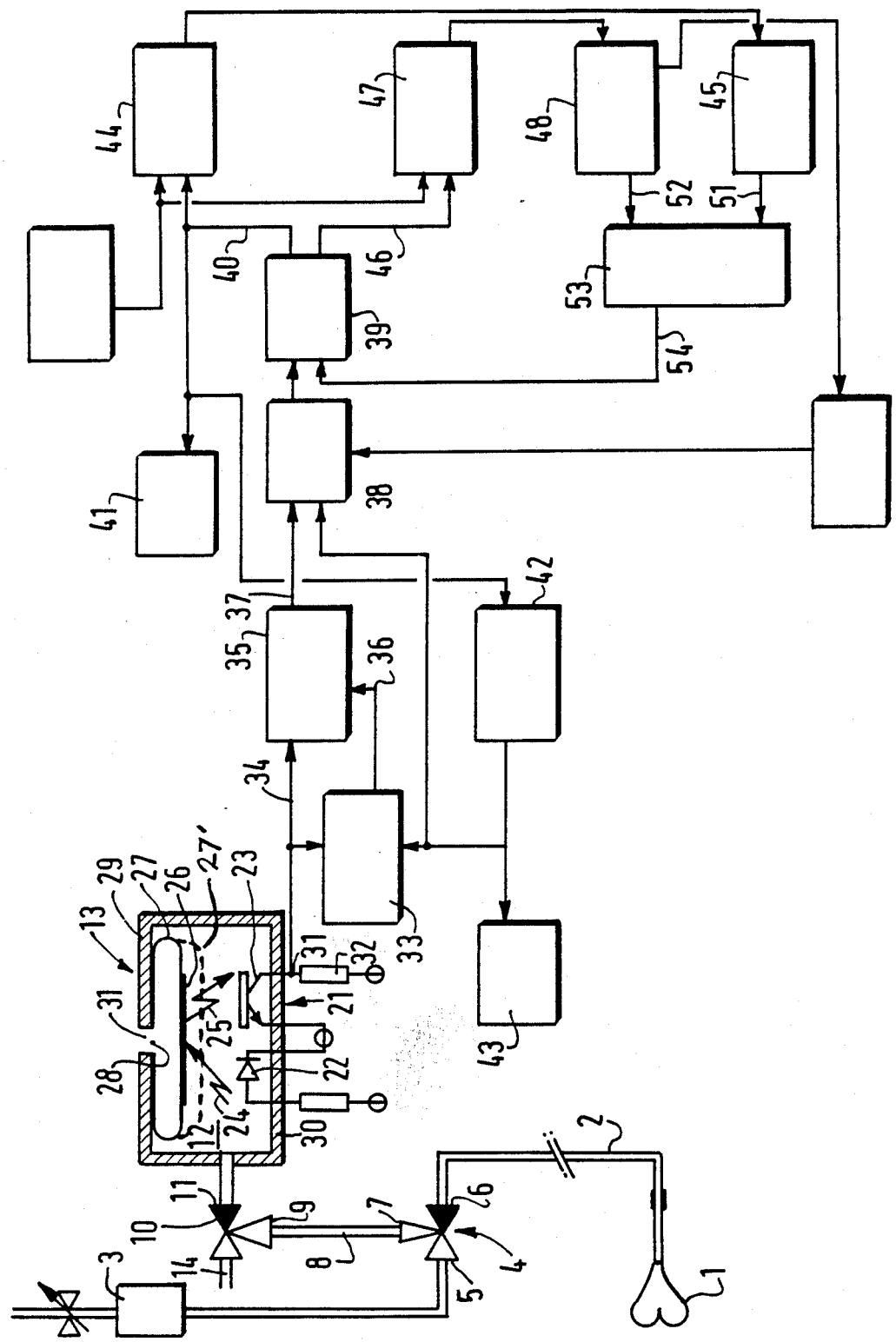

PROCESS AND DEVICE FOR SUPPLYING RESPIRATORY OXYGEN

BACKGROUND OF THE INVENTION

Field of the Invention

The present invention relates to the additional supply of respiratory oxygen to a patient. This supply is provided in addition to the natural supply of air of the atmosphere only during a part of the inspiratory phase. The additional supply is initiated by the detection or the anticipated detection, of the start of an inspiratory phase relative to the atmospheric pressure in a detecting chamber having an electronic sensor.

DESCRIPTION OF THE PRIOR ART

French patent No. 84 17,236 discloses an electronic sensor with a windbag equipped with a strip which is interposed in the optical path upon an inspiratory depression. This brings about, for a given lapse of time, the opening of an electrically controlled valve supplying breathable gas. This mode of operation is capable of providing good sensitivity provided there is a fine adjustment in the position of the various cooperating parts, since adjusment is generally necessary from time to time.

OBJECT OF THE PRESENT INVENTION

An object of the present invention is to improve this type of supply by providing arrangements which result in improved sensitivity and automatic calibration without the requirement of subsequent adjustments during the course of operation.

"SUMMARY"

In the present invention, the opto-electronic detection is effected by a sensor of the type employing a reflection on a reflector placed against a wall of the windbag, which is opposed to the fixing wall of the windbag, a variation in the current of the sensor upon a reduction in the distance between the sensor and the windbag due to an expansion of the windbag resulting from a start, or an anticipated start, of an inspiratary phase brings about a predetermined supply of respiratory gas. There is, during each expiratory phase, storage of an output reference voltage of the sensor representing the atmospheric pressure. The supply of breathable gas is brought about by comparison of this reference voltage with a voltage signal representing a drop in the inspiratory pressure indicating the end of an expiratory phase or the start of an inspiratory phase.

In this way, because of the repeated comparison between two voltages whose difference indicates the start of an inspiratory phase, a correct operation can be ensured. Even if the appliance employed undergoes a change in its own characteristics over a period of time.

The invention also relates to a device for providing an additional supply of breathable oxygen of the type comprising a supply conduit of a respiratory mask or a tracheal probe, incorporating a three-way electrically controlled valve whose third way is connected to the third way of another electrically controlled valve for putting in communication with the air of the atmosphere a detector having an opto-electronic sensor associated with a windbag, means for cyclically controlling the breathable oxygen supply valve and an air communication valve, in which the opto-electronic sensor is of the type employing a reflection on a reflector placed against a wall of the windbag which is opposed to a fixing wall of the windbag. In a preferred embodiment of the present invention, the cyclic control means of the valves for supplying breathable oxygen and for communication with the air comprises: means for producing an electronic voltage representing the pressure in the chamber of the detector; means for storing the voltage during the communication of the detector with the air, or reference voltage; means for effecting a comparison between the stored reference voltage and the instantaneous voltage representing the pressure in the chamber of the detector. The comparing means causing the valve to open to supply breathable oxygen, when there is a difference with the reference voltage indicating the start, or the anticipated start, of an inspiratory phase, and further causing a deferred opening of the valve, beyond the supply phase, for putting the detector in communication with the air of the atmosphere.

BRIEF DESCRIPTION OF THE DRAWING

The features and advantages of the invention will be more clear from the following detailed description which is given, by way of example with reference to the accompanying drawing in which the sole figure is represents a diagrammatic representation of a preferred embodiment of the invention.

DETAILED DESCRIPTION OF CERTAIN PREFERRED EMBODIMENTS

A respiratory mask 1 is connected through a conduit 2 to a buffer-chamber 3 interposed therebetween is a three way electrically controlled supply valve 4. The buffer-chamber 3 is connected through an adjustable calibrated orifice to a concentrator (not shown) which concentrates the oxygen in the ambient atmosphere. Such concentrators are advantageously of the adsorption type.

The electrically controlled valve 4 has two operating positions, namely:

(1) A first supply position in which the ways 5 and 6 communicate with each other, while way 7 is closed (this position supplies the mask 1 with superoxygenated breathable gas through the conduit 2 from the buffer-chamber 3); and (2) A second standby position in which the ways 6 and 7 communicate with each other, while the way 5 is closed (In this position, the signal of the start of the inspiration or the end of the expiration will be transmitted).

The way 7, of the electrically controlled valve 4, is connected through a pipe 8 to a third way 9 of an electrically controlled detecting valve 10. The first way 11, of detecting valve 10 communicates with an inner chamber 12 of an opto-electronic detector 13. A second way 14 of detecting valve 10 communicates with the open air.

The detecting valve 10 has two operating positions, namely:

(1) A first position for awaiting the signal of the end of the expiration or the start of the inspiration, in which the ways 9 and 11 communicate with each other, (the signal is a depression conveyed from the patient's mask 1 via the conduit 2, the ways 6 and 7 of the electrically controlled valve 4, the ways 9 and 11 of the electrically controlled valve 10, to chamber 12 of detector 13), in this position the way 14 is closed;

(2) a second position for receiving the atmospheric pressure in which the ways 11 and 14 communicate with each other, while the way 9 is closed, (in this position, the chamber 12 of the detector 13 is brought to atmospheric pressure.)

Placed in the chamber 12 of the detector 13 are the detecting elements.

A reflection sensor 21, comprising an optical emitter 22 associated with an optical receiver 23 is disposed, the optical beam is emitted at 24 in the upward direction. This beam, reflected at 25 by a planar reflector 26, is received by the receiver 23 at the end of its downward return path. The planar reflector 26 is mounted on the bottom wall of; a windbag 27. The windbag 27 has a thin, flexible, very light wall with a single opening 28.

The windbag 27 is fixed in a sealed manner against an upper wall 29 of the detector 13 so that the planar reflector 26 is in a horizontal position parallel to the bottom wall 30 of the detector 13. The opening 28 is directly in line with an opening 31 in the detector chamber 12. Thus, the interior of the windbag 27 is always at atmospheric pressure.

When detecting valve 10 is in a position for receiving atmospheric pressure through ways 8 and 11, the windbag 27 is in the position shown in full lines.

When the detecting valve 10 is in a position awaiting an inspiration signal through ways 9 and 11 and ways 6 and 7 of the electrically controlled valve 4, the windbag 27 maintains the same configuration as long as the decompression signal due to an end of an expiration or a start of an inspiration has not reached the chamber 12. As soon as the chamber 12 is subjected to the drop in pressure, the windbag 27 almost instantaneously assumes a more elongated shape 27' owing to the higher pressure prevailing inside the bag.

In the retracted position of the windbag 27, the path of the optical signal is the longest and the sensor 23 receives a relatively weak optical flux.

In the elongated position 27' of the windbag 27, the path of the optical signal is shorter and the sensor 23 receives a relatively strong optical flux since there are fewer optical losses.

It is this difference in the optical fluxes received by the sensor 23 which results in the regulated operation of the supply of breathable gas.

The signal from the sensor is applied to the terminal 31 of a resistor 32 which determines a voltage there.

The voltage at the terminal 31 is applied to a memory device 33 and to an input 34 of an analog comparator 35 whose other input 36 receives a signal from the memory device 33.

The signal at the output 37 of the analog comparator 35 is applied to an electronic gate 38 controlling a bistable element 39 having an output 40 the output 40 goes to a control circuit 41 for the electrically controlled valve 4 on one hand, to a time delay device 42 and thence to the memory device 33 and to a device 43 controlling the electrically controlled valve 10 on the other hand, and lastly to an electronic gate 44 controlling an electronic counter 45.

A second output 46 of the bistable element 39 is connected to an electronic gate 47 controlling a counter 48 whose counting speed is notably lower than the counting speed of the counter 45.

The counting signals of the counters 45 and 48 are applied to inputs 51, 52 of an analog comparator 53 whose signal at an output 54 is applied to a second input of the bistable element 39.

A clock device 55 ensures the actual operation of the counters 45 and 48.

The installation just described operates in the following manner:

At rest, when the mask 1 is not connected to the patient, the electrically controlled valve 4 stops the supply. Way 5 is closed and ways 6 and 7 are interconnected, while the detecting valve 10 is in the condition awaiting the signal corresponding to the end of an expiration or the start of an inspiration (i.e. way 14 is closed and ways 9 and 11 are interconnected). Consequently, the chamber 12 of the detector 13 is connected to the mask 1 and, as the latter is not used, the chamber 12 is at atmospheric pressure and the windbag 27 is in the retracted position. The voltage at the terminal 31 represents the atmospheric pressure and is the reference voltage which may be stored in the memory device 33.

Upon placing the mask 1 in position, the inspiratory effort of the patient transmitted through the electrically controlled valve 14 (through ways 6 and 7) and the detecting valve 10 (through ways 9 and 11) results in a depression in the chamber 12 of the detector 13 and causes the immediate expansion of the windbag 27 to the state 27'. The sensor 21 records a stronger optical flux so that the potential at the terminal 31 varies in a direction which causes the output 37 of the analog comparator 35 to change to a positive polarity from a previous negative polarity. This change of polarity modifies the state of the bistable element 39 whose output 40 becomes positive, which then acts to:

(1) open the electrically controlled supply valve 4 through the device 41 (ways 5 and 6 communicate with each other and way 7 is closed) which sends breathable gas to the patient in the course of inspiration;

(2) actuate the time delay device 42 which immediately causes the operation of the control device 43 of the detecting valve 10 for putting ways 11 and 14 in communication with each other so that the chamber 12 of the sensor 13 returns to atmospheric pressure; and (3) simultaneously, to bring into action the memory device 33 which stores an instantaneous atmospheric pressure just before a following inspiration on the part of the patient.

After an adjustable given lapse of time, when the counters 45 and 48 have equal output signals (a more detailed description of the operation will be given hereinafter), the comparator 53 resets the bistable element 39 whose output 40 changes to zero potential which immediately causes, through the device 41, the stoppage of the supply of breathable gas (way 5 closed, ways 6 and 7 in communication with each other). Simultaneously, the time delay device 42 causes a delayed actuation (on the order of a second) of the device 43 controlling the detecting valve 10 which remains in the same position and a delayed actuation of the memory device 35.

At the end of the delayed phase, the time delay device 42 causes actuation of the memory device 33 (stored reference voltage) and the switching of detecting valve 10 which results in the setting of the standby position (ways 9 and 11 in communication with each other) which awaits a new inspiratory signal from the patient.

The cycle just described can then be repeated.

Details will now be given as to how the duration of the breathing gas supply phase is determined. This phase occurs during a fraction of the inspiratory phase of the patient.

Throughout the phase of the supply of breathable gas, when the output 46 of the bistable element 39 is positive, the counter 48 is in operation, while the counter 45 is inoperative. At the beginning of an inspiratory phase of the patient, the bistable element 39 changes state, the output 40 becomes positive, and the output 46 becomes zero. The counter 48 stops, while the counter 45 starts to operate. When the output signals of the counters 45, 48 are equal, the comparator 53 causes the bistable element 39 to change state so that the output 40 returns to zero (resulting in immediate closure of the supply electrically controlled valve 4) and the output 46 becomes positive with the aforementioned consequences.

It will be understood that the duration of the supply of breathable gas depends on the duration of the phase in which no breathable gas is supplied, which is directly related to the duration of the expiratory phase and, to a certain extent, to the respiratory frequency of the patient.

We claim:

1. A method for supplying a patient having inspiratory and expiratory phases with respiratory oxygen, comprising the following steps:
   (a) providing an oxygen supply during only a part of an inspiratory phase;
   (b) initiating said inspiratory phase by detecting a reduction in pressure in a detecting chamber;
   (c) modifying current from a sensor means in response to an increase in optical flux due to a reduction in the distance between said sensor means and a reflector means which is due to an expansion of a windbag resulting from a pressure drop in said detecting chamber to insure a supply of respiratory gas;
   (d) storing, in a memory, during each inspiratory-expiratory phase, a reference output voltage of said sensor means representing the atmospheric pressure; and
   (e) causing the delivery of breathable gas to the patient at the start of the patient's inspiratory phase detected by comparison of said reference voltage with a voltage representing an inspiratory depression.

2. A process according to claim 1, further comprising the following additional step:
   regulating the duration of the supply of breathable gas as a direct function of the duration of the preceding expiratory phase.

3. A process according to claim 1, further comprising the following step:
   said detecting chamber in communication with the ambient atmosphere to create a reference voltage following a delay after the end of an operation during which breathable oxygen was supplied.

4. A device for supplying breathable oxygen, comprising:
   (a) gas delivery means;
   (b) a supply conduit connected to said delivery means including first valve means for supplying breathable oxygen, said valve means having three ways;
   (c) a detecting chamber having an opening therein, said opening communicating with the atmosphere, wherein said detecting chamber includes, a flexible windbag having an upper wall with an opening therein, wherein said upper wall is fixed to said detecting chamber such that said windbag opening is aligned with said detecting chamber opening thereby permitting said windbag to communicate with the atmosphere, and said windbag further including a lower wall opposed to said upper wall, and sensor means having beam emitter means, reflector means placed against said lower wall of said windbag for receiving a beam emitted by said beam emitter means, and beam receiver means mounted relative to said detecting chamber at a distance from said reflector means for receiving a beam reflected by said reflector means;
   (d) second valve means connected to said detecting chamber, said second valve means having three ways, one of said ways putting said detecting chamber in communication with air of the atmosphere, the third way of said first valve means being connected to a third way of said second valve means; and
   (e) means for cyclically controlling said first valve means and said second valve means.

5. A supply device according to claim 4, wherein the means for cyclically controlling said first valve means and said second valve means comprises:
   (a) means for creating an electronic reference voltage representing the pressure in said detecting chamber;
   (b) memory means for storing said reference voltage in memory;
   (c) comparison means for effecting a comparison between said stored reference voltage and an instantaneous voltage representing the pressure in the detecting chamber, said comparison means causing, when there is a difference between said reference voltage and said instantaneous voltage, the immediate opening of said first valve means and a deferred opening of said second valve means 6. A device according to claim 4, further comprising:
   (a) means for regulating the duration of the supply for breathable oxygen including: means for counting the durations of supply and non-supply of breathable oxygen and means for comparing said durations; and
   (b) means for causing a stoppage of said first valve means responsive to the action of said duration comparing means.

7. A device according to claim 5, further comprising:
   (a) means for regulating the duration of the supply of breathable oxygen including: means for counting the durations of the supply and non-supply of breathable oxygen and means for comparing said durations; and
   (b) means for causing a stoppage of said first valve means responsive to the action of said duration comparing means.

8. An apparatus for supplying breathable oxygen, comprising:
   (a) gas delivery means;
   (b) a source of breathable gas communicating with an accumulator-buffer including: an outlet, a supply conduit connecting said outlet to said gas delivery means and a device having: a first electronically controlled valve, said valve having three ways and adapted to be inserted into said conduit;
   (c) a detecting chamber having an opening therein, said opening communicating with the atmosphere, wherein said detecting chamber includes, a flexible windbag having an upper wall with an opening therein, wherein said upper wall is fixed to said detecting chamber such that said windbag opening is aligned with said detecting chamber opening thereby permitting said windbag to communicate with the atmosphere, and said windbag further including a lower wall opposed to said upper wall, and an opto-electronic sensor comprising: beam emitter means, reflector means placed against said lower wall of said windbag for receiving a beam emitted from said beam emitter means, and beam receiver means mounted at a distance from said reflector means for receiving the beam reflected by said reflector means;

(d) a second electrically controlled valve connected to said detecting chamber, said second electrically controlled valve having three ways for putting said detecting chamber in communication with air of the atmosphere, a third way of said first electrically controlled valve being connected to a third way of said second electrically controlled valve; and (e) means for cyclically controlling said first valve and said second valve.

9. A process according to claim 1, wherein said reference voltage is compared with a voltage representing the end of an expiratory phase.

10. A device according to claim 6, wherein said gas delivery means comprises a breathing mask.

11. A device according to claim 6, wherein said gas delivery means comprises a tracheal probe.

12. A device according to claim 8, wherein said gas delivery means comprises a breathing mask.

13. A device according to claim 8, wherein said gas delivery means comprises a tracheal probe.

* * * * *